United States Patent
Koike

(10) Patent No.: US 6,306,417 B2
(45) Date of Patent: Oct. 23, 2001

(54) WETTABLE OR WATER-SOLUBLE GRANULAR AGROCHEMICAL COMPOSITION

(75) Inventor: Masahiko Koike, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/341,811

(22) PCT Filed: Feb. 9, 1998

(86) PCT No.: PCT/JP98/00521

§ 371 Date: Jul. 19, 1999

§ 102(e) Date: Jul. 19, 1999

(87) PCT Pub. No.: WO98/34483

PCT Pub. Date: Aug. 13, 1998

(30) Foreign Application Priority Data

Feb. 10, 1997 (JP) .................................................. 9-026954

(51) Int. Cl.$^7$ .................................................. A01N 25/14
(52) U.S. Cl. .......................... 424/417; 424/406; 424/409; 424/421; 514/365; 504/266
(58) Field of Search ............................ 514/365; 424/405, 424/406, 409, 417–421; 504/266

(56) References Cited

U.S. PATENT DOCUMENTS 5,543,385   8/1996   Rochling et al. ..................... 504/127

FOREIGN PATENT DOCUMENTS

| | | |
|---|---|---|
| A-2334345 | 7/1973 | (DE) . |
| A-375907 | 7/1990 | (EP) . |
| A-376279 | 7/1990 | (EP) . |
| A-0413267 | 2/1991 | (EP) . |
| A-418199 | 3/1991 | (EP) . |
| A-425978 | 5/1991 | (EP) . |
| A-0447056 | 9/1991 | (EP) . |
| A-60-126201 | 7/1985 | (JP) . |
| A-61-027902 | 2/1986 | (JP) . |
| A-4-108704 | 4/1992 | (JP) . |
| A-4-112804 | 4/1992 | (JP) . |
| A-4-112805 | 4/1992 | (JP) . |
| A-4-120007 | 4/1992 | (JP) . |
| A-5-279211 | 10/1993 | (JP) . |
| A-6-92803 | 4/1994 | (JP) . |
| A-6-128102 | 5/1994 | (JP) . |
| A-7-291804 | 11/1995 | (JP) . |

Primary Examiner—Neil S. Levy
(74) Attorney, Agent, or Firm—Wenderoth, Lind & Ponack, L.L.P.

(57) ABSTRACT

The present invention provides a wettable or water-soluble granular agrochemical composition which comprises a guanidine derivative of the formula:

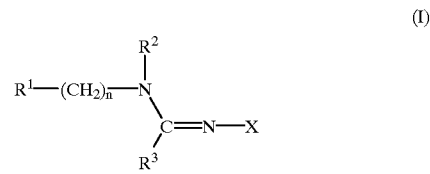

(I)

wherein $R^1$ represents a homocyclic or heterocyclic group which may optionally be substituted; n is 0 or 1; $R^2$ represents hydrogen or a hydrocarbon group which may optionally be substituted; $R^3$ represents a primary, secondary, or tertiary amino group; X represents an electron attractive group; or a salt thereof, an alkenylsulfonate and a carrier. The agrochemical composition has excellent disintegrability and dispersibility in water.

5 Claims, No Drawings

WETTABLE OR WATER-SOLUBLE GRANULAR AGROCHEMICAL COMPOSITION

This application is a 371 of PCT/JP98/00521 filed Feb. 9, 1998.

TECHNICAL FIELD

The present invention relates to a wettable or water-soluble granular agrochemical composition with excellent disintegrability in water and high dispersion stability.

BACKGROUND ART

Wettable granular agrochemical formulations are agrochemical granules which can be completely or easily dispersed or dissolved in water and, as such, are superior to earlier wettable powders in terms of ease of handling, ease of weighing, dust prevention, and convenience in application. However, manufacture of such granular preparations according to the conventional production recipes for wettable powders causes various troubles such as poor disintegrability in water, thus failing to give a stable dispersion.

As excellent pesticidal agents, JP-A 157308/1991 discloses a large number of guanidine derivatives, typically the compound of the following formula (II), and their compositions.

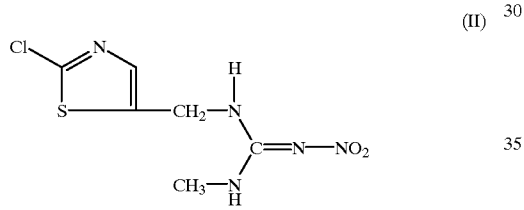

Moreover, certain guanidine derivatives and agrochemical formulations containing them (dusts, wettable powders, granules, etc.) are described in JP-A 28860/1990, JP-A 109374/1991 and JP-A 200768/1991.

The above-mentioned compound (II) is poorly soluble in water with a solubility of not more than 0.0003 g/ml in water at 20° C. and the conventional wettable powders have a drawback that they do not disintegrate well in water, thus failing to give a stable dispersion.

Therefore, in order that the compound (II) shows a pesticidal action more efficiently, development of a wettable or soluble granular agrochemical composition with excellent disintegrability and dispersibility in water has been awaited in earnest.

DISCLOSURE OF INVENTION

The inventors of the present invention have made much research and discovered surprisingly that, in a wettable or soluble granular agrochemical formulation containing a guanidine derivative such as said compound (II), incorporation of an alkenylsulfonate and a carrier such as lactose, ammonium sulfate, sodium hydrogen carbonate or diatomaceous earth as a carrier results in remarkable improvements in disintegrability and dispersibility in water. The inventors have made further research on the basis of the above findings and have completed the present invention.

Namely, the present invention relates to:
(1) a wettable or water-soluble granular agrochemical composition which comprises a guanidine derivative of the formula:

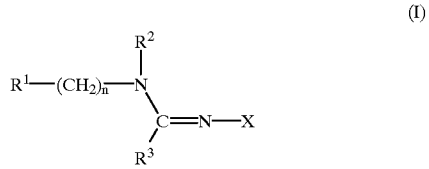

wherein
$R^1$ represents a homocyclic or heterocyclic group which may optionally be substituted; n is 0 or 1;
$R^2$ represents hydrogen or a hydrocarbon group which may optionally be substituted; $R^3$ represents a primary, secondary, or tertiary amino group; X represents an electron attractive group; or a salt thereof, an alkenylsulfonate and a carrier,
(2) the agrochemical composition as described in (1) above, wherein the guanidine derivative of the formula (I) is the compound of the formula:

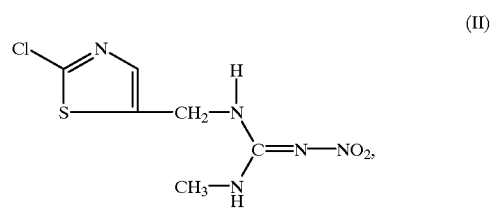

(3) the agrochemical composition as described in (1) above, wherein the carrier is one or more carriers selected from the group consisting of lactose, ammonium sulfate, sodium hydrogen carbonate, and diatomaceous earth,
(4) a wettable granular agrochemical composition which comprises 30 to 85 weight % of the guanidine derivative of the formula (I) as described in (1) above, or a salt thereof, 0.1 to 15 weight % of an alkenylsulfonate and 10 to 70 weight % of a carrier to the total composition,
(5) a water-soluble granular agrochemical composition which comprises 5 to 60 weight % of the guanidine derivative of the formula (I) as described in (1) above, or a salt thereof, 0.1 to 15 weight % of an alkenylsulfonate and 25 to 95 weight % of a carrier to the total composition,
(6) a method for producing the agrochemical composition as described in (1) above, which comprises mixing the guanidine derivative of the formula (I) as described in (1) above, or a salt thereof and an alkenylsulfonate with a carrier, and granulating them, and
(7) a method for controlling a pest which comprises diluting the agrochemical composition as described in (1) above with water and scattering the thus diluted composition in a field.

BEST MODE FOR CARRYING OUT THE INVENTION

The guanidine derivative (I) for use in the wettable or water-soluble granular agrochemical composition (hereinafter sometimes referred to briefly as "agrochemical composition") of the present invention occurs as geometrical isomers, namely cis[Z (zusammen or together)]- and trans[E (entgegen or opposite)]-isomers, in respect of the geometrical orientation of X, and when $R^2$ is hydrogen and $R^1$ is a primary or secondary amino group, then tautomers are formed theoretically. All of such isomers are also included in the category of guanidine compound (I) or its salt.

The homocyclic or heterocyclic group of $R^1$ is a cyclic group containing the same atoms only or a cyclic group containing two or more different atoms, i.e., a cyclic hydrocarbon group or a heterocyclic group, respectively.

The cyclic hydrocarbon group of $R^1$ includes a $C_{3-14}$ cyclic hydrocarbon group, specifically include a non-aromatic cyclic hydrocarbon group such as a $C_{3-8}$ cycloalkyl group, e.g. cyclopropyl, cyclobutyl, cyclopentyl or cyclohexyl; and a $C_{3-8}$ cycloalkenyl group, e.g. cyclopropenyl, 1-cyclopentenyl, 1-cyclohexenyl, 2-cyclohexenyl, 1,4-cyclohexadienyl; and an aromatic cyclic hydrocarbon group such as a $C_{6-4}$ aryl group, e.g. phenyl, naphthyl such as 1- or 2-naphthyl, anthryl such as 1-, 2- or 9-anthryl, phenanthryl such as 1-, 2-, 3-, 4- or 9-phenanthryl or azulenyl such as 1-, 2-, 4-, 5- or 6-azulenyl. The preferred cyclic hydrocarbon groups are aromatic ones, e.g. $C_{6-14}$ aryl groups such as phenyl, etc.

The heterocyclic group of $R^1$ includes a 5- to 8-membered ring group containing one to five hetero atoms selected from oxygen atom, sulfur atom and nitrogen atom and its condensed ring group with a 5- to 8-membered carbon ring or a 5- to 8-membered heterocyclic ring. Examples of the heterocyclic group are thienyl (e.g. 2- or 3-thienyl), furyl (e.g. 2- or 3-furyl), pyrrolyl (e.g. 2- or 3-pyrrolyl), pyridyl (e.g. 2-, 3- or 4-pyridyl), oxazolyl (e.g. 2-, 4- or 5-oxazolyl), thiazolyl (e.g. 2-, 4- or 5-thiazolyl), pyrazolyl (e.g. 3-, 4- or 5-pyrazolyl), imidazolyl (e.g. 2-, 4- or 5-imidazolyl), isoxazolyl (e.g. 3-, 4- or 5-isoxazolyl), isothiazolyl (e.g. 3-, 4- or 5-isothiazolyl), oxadiazolyl (e.g. 3- or 5-(1,2,4-oxadiazolyl), 1,3,4-oxadiazolyl), thiadiazolyl (e.g. 3- or 5-(1,2,4-thiadiazolyl), 1,3,4-thiadiazolyl, 4- or 5-(1,2,3-thiadiazolyl), 1,2,5-thiadiazolyl), triazolyl (e.g. 1,2,3-triazolyl, 1,2,4-triazolyl), tetrazolyl (e.g. 1H- or 2H-tetrazolyl), pyridyl in which the nitrogen atom is oxidized (e.g. N-oxido-2-, 3- or 4-pyridyl), pyrimidinyl (e.g. 2-, 4- or 5-pyrimidinyl), pyrimidinyl in which one or both of the nitrogen atoms are oxidized (e.g. N-oxido-2-, 4- or 5-pyrimidinyl), pyridazinyl (e.g. 3- or 4-pyridazinyl), pyrazinyl, pyridazinyl in which one or both of the nitrogen atoms are oxidized (e.g. N-oxido-3- or 4-pyridazinyl), benzofuryl, benzothiazolyl, benzoxazolyl, triazinyl, oxotriazinyl, tetrazolo[1,5-b]pyridazinyl, triazolo[$4,^5$-b]pyridazinyl, oxoimidazinyl, dioxotriazinyl, pyrrolidinyl, piperidinyl, pyranyl, thiopyranyl, oxadinyl (e.g. 1,4-oxadinyl), morpholinyl, thiazinyl (e.g. 1,4-thiazinyl, 1,3-thiazinyl), piperazinyl, benzimidazolyl, quinolyl, isoquinolyl, cinnolinyl, phthalazinyl, quinazolinyl, quinoxalinyl, indolidinyl, quinolidinyl, naphthyridinyl (e.g. 1,8-naphthyridinyl), purinyl, pteridinyl, dibenzofuranyl, carbazolyl, acridinyl, phenanthridinyl, phenazinyl, phenothiadinyl or phenoxazinyl. Preferred heterocyclic groups are 5- or 6-membered nitrogen-containing heterocyclic groups such as pyridyl (e.g. 2-, 3- or 4-pyridyl) or thiazolyl (e.g. 2-, 4- or 5-thiazolyl). The homocyclic or heterocyclic group of $R^1$ may possess one to five (preferably one) substituents which are the same or different. Examples of the substituents are a $C_{1-15}$ alkyl group such as methyl, ethyl, propyl, isopropyl, butyl, isobutyl, s-butyl, t-butyl, pentyl, hexyl, heptyl, octyl, nonyl, decyl, undecyl, dodecyl tridecyl, tetradecyl or pentadecyl; a $C_{3-10}$ cycloalkyl group such as cyclopropyl, cyclobutyl, cyclopentyl or cyclohexyl; a $C_{2-10}$ alkenyl group such as vinyl, allyl, 2-methylallyl, 2-butenyl, 3-butenyl or 3-octenyl; a $C_{2-10}$ alkynyl group such as ethynyl, 2-propynyl or 3-hexynyl; a $C_{3-10}$ cycloalkenyl group such as cyclopropenyl, cyclopentenyl or cyclohexenyl; a $C_{6-14}$ aryl group such as phenyl or naphthyl; a $C_{7-19}$ aralkyl group such as phenyl-$C_{1-4}$ alkyl (e.g. benzyl or phenylethyl); nitro group; hydroxy group; mercapto group; oxo group; thioxo group; cyano group; carbamoyl group; carboxyl group; a $C_{1-4}$ alkoxycarbonyl group such as methoxycarbonyl or ethoxycarbonyl; sulfo group; a halogen atom such as fluorine, chlorine, bromine or iodine; a $C_{1-4}$ alkoxy group such as methoxy, ethoxy, propoxy, isopropoxy, butoxy, isobutoxy, s-butoxy or t-butoxy; a $C_{6-14}$ aryloxy group such as phenoxy; a $C_{1-4}$ alkylthio group such as methylthio, ethylthio, n-propylthio, isopropylthio, n-butylthio or t-butylthio;

a $C_{6-14}$ arylthio group such as phenylthio; a $C_{1-4}$ alkylsulfinyl group such as methylsulfinyl or ethylsulfinyl; a $C_{6-14}$ arylsulfinyl group such as phenylsulfinyl; a $C_{1-4}$ alkylsulfonyl group such as methylsulfonyl or ethylsulfonyl; a $C_{6-14}$ arylsulfonyl group such as phenylsulfonyl; amino group; a $C_{2-6}$ acylamino group such as a $C_{2-6}$ alkanoylamino group (e.g. acetylamino or propionylamino); a mono- or di-$C_{1-4}$ alkylamino group such as methylamino, ethylamino, n-propylamino, isopropylamino, n-butylamino, dimethylamino or diethylamino; a $C_{3-6}$ cycloalkylamino group such as cyclohexylamino; a $C_{6-14}$ arylamino group such as anilino; a $C_{2-4}$ acyl such as a $C_{7-4}$ alkanoyl group (e.g. acetyl); a $C_{6-14}$ arylcarbonyl group such as benzoyl; and a 5- or 6-membered heterocyclic group containing one to four hetero atoms selected from oxygen, sulfur and nitrogen or a condensed ring group thereof with a benzene ring, such as thienyl (e.g. 2- or 3-thienyl), furyl (e.g. 2- or 3-furyl), pyrazolyl (e.g. 3-, 4- or 5-pyrazolyl), thiazolyl (e.g. 2-, 4- or 5-thiazolyl), isothiazolyl (e.g. 3-, 4- or 5-isothiazolyl), oxazolyl (e.g. 2-, 4- or 5-oxazolyl), isoxazolyl (e.g. 3-, 4- or 5-isoxazolyl), imidazolyl (e.g. 2-, 4- or 5- imidazolyl), triazolyl (e.g. 1,2,3- or 1,2,4-triazolyl), tetrazolyl (e.g. 1H- or 2H-tetrazolyl), pyridyl (e.g. 2-, 3- or 4-pyridyl), pyrimidinyl (e.g. 2-, 4- or 5-pyrimidinyl), pyridazinyl (e.g. 3- or 4-pyridazinyl), quinolyl, isoquinolyl or indolyl. When the substituent is e.g., a $C_{6-14}$ aryl, $C_{7-19}$ aralkyl, $C_{3-10}$ cycloalkyl, $C_{3-10}$ cycloalkenyl, $C_{6-14}$ aryloxy, $C_{6-14}$ arylthio, $C_{6-14}$ arylsulfinyl, $C_{6-14}$ arylsulfonyl, $C_{6-14}$ arylamino or heterocyclic group, it may be further substituted by one to five of halogen atom; hydroxy group; $C_{1-4}$ alkyl group such as methyl, ethyl, propyl, isopropyl, butyl, isobutyl, s-butyl or t-butyl; $C_{2-4}$ alkenyl group such as vinyl, allyl or 2-methylallyl; $C_{2-4}$ alkynyl group such as ethynyl or 2-propynyl; $C_{6-14}$ aryl group such as phenyl or naphthyl; $C_{1-4}$ alkoxy group; phenoxy group; $C_{1-4}$ alkylthio group or phenylthio group. When the substituent is a $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono- or di-$C_{1-4}$ alkylamino or $C_{3-6}$ cycloalkylamino group, it may be further substituted by one to five of halogen atom, hydroxy group, $C_{1-4}$ alkoxy group or $C_{1-4}$ alkylthio group.

Preferred examples of $R^1$ are 5- or 6-membered nitrogen-containing heterocyclic groups such as pyridyl or thiazolyl which may be substituted by one or two halogens. Especially, thiazolyl which is substituted by a chlorine atom (e.g. 2-chloro-5-thiazolyl, etc.) is preferable.

The symbol "n" denotes 0 or 1, preferably 1.

The hydrocarbon group in the "optionally substituted hydrocarbon group" of $R^2$ includes $C_{1-19}$ hydrocarbon groups such as $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-14}$ aryl and $C_{7-19}$ aralkyl groups which are mentioned with respect to $R^1$.

Those mentioned as the substituents on the homocyclic or heterocyclic group of $R^1$ are used as the substituents on the "optionally substituted hydrocarbon group".

Preferred examples of $R^2$ are hydrogen atom and a $C_{1-4}$ alkyl group such as methyl, ethyl or propyl. Especially, hydrogen atom is preferable.

$R^3$ denotes a primary, secondary or tertiary amino group, which can be represented by the formula:

wherein $R^4$ and $R^5$ are, the same or different, a hydrogen atom or an optionally substituted hydrocarbon group or both $R^4$ and $R^5$ are combined together with the adjacent nitrogen atom to form a cyclic amino group. Here, the primary amino group is an unsubstituted amino group in case where $R^4$ and $R^5$ in the above formula are a hydrogen atom; the secondary amino group is mono-substituted amino group in case where either one of $R^4$ and $R^5$ is hydrogen atom; and the tertiary amino group is disubstituted amino group in case where neither of $R^4$ and $R^5$ is hydrogen atom. The optionally substituted hydrocarbon groups mentioned with respect to $R^2$ are used as the optionally substituted hydrocarbon groups for $R^4$ and $R^5$.

$R^4$ and $R^5$ are preferably a $C_{1-15}$ alkyl group, especially a $C_{1-6}$ alkyl group.

Examples of the cyclic amino group which are formed by $R^4$ and $R^5$ together with the adjacent nitrogen atom are 3- to 8-membered cyclic amino groups such as aziridino, azetidino, pyrrolidino, piperidino, morpholino and thiomorpholino groups. Preferred examples of $R^3$ are an unsubstituted amino group; a mono-$C_{1-4}$ alkylamino group such as methylamino, ethylamino or propylamino; a di-$C_{1-4}$ alkylamino group such as dimethylamino or ethylmethylamino and a $C_{1-4}$ acylamino group such as a $C_{1-4}$ alkanoylamino group (e.g. formamido, N-methylformamido or acetamido). Especially, a mono-$C_{1-4}$ alkylamino group such as methylamino is preferable.

Examples of the electron attractive group of X are cyano, nitro, an alkoxycarbonyl group (e.g., $C_{1-4}$ alkoxycarbonyl such as methoxycarbonyl or ethoxycarbonyl), hydroxycarbonyl (carboxyl), a $C_{6-10}$ aryloxycarbonyl group (e.g., phenoxycarbonyl), a heterocycle-oxycarbonyl group (as the heterocyclic group, the above-mentioned heterocyclic group for $R^1$ being applicable to this group, thus specifically pyridyloxycarbonyl or thienyloxycarbonyl), a $C_{1-4}$ alkylsulfonyl group which may be substituted by 1 to 3 halogen atoms such as fluorine, chlorine or bromine (e.g., methylsulfonyl, trifluoromethylsulfonyl, ethylsulfonyl), sulfamoyl, a di-$C_{1-4}$ alkoxyphosphoryl group (e.g., diethoxyphosphoryl), a $C_{1-4}$ acyl group such as a $C_{1-4}$ alkanoyl group which may be substituted by 1 to 3 halogen atoms such as chlorine, bromine or fluorine (e.g., acetyl, trichloroacetyl or trifluoroacetyl), a $C_{6-10}$ aryl-carbonyl group (e.g., benzoyl), carbamoyl or a $C_{1-4}$ alkylsulfonylthiocarbamoyl group (e.g., methylsulfonylthiocarbamoyl). Preferred examples of the electron attractive group are a nitro group, a trifluoroacetyl group and a cyano group. Especially preferred is a nitro group.

Preferred example of the guanidine derivative (I) or its salt is a compound of the formula ($I^b$)

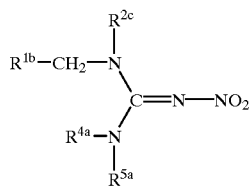

wherein $R^{1b}$ is a pyridyl group, a halogenopyridyl group or a halogenothiazolyl group, $R^{2c}$, $R^{4a}$ and $R^{5a}$ are, the same or different, hydrogen atom, or a methyl, ethyl, formyl or acetyl group, or its salt. Specifically, $R^{1b}$ of the formula ($I^b$) includes 3-pyridyl, a halogenopyridyl group such as 6-chloro-3-pyridyl, 6-bromo-3-pyridyl or 5-bromo-3-pyridyl or a halogenothiazolyl group such as 2-chloro-5-thiazolyl or 2-bromo-5-thiazolyl.

Among them, $R^{1b}$ is preferably 2-chloro-5-thiazolyl.

Especially preferred example of the guanidine derivative (I) is the compound of the formula (II):

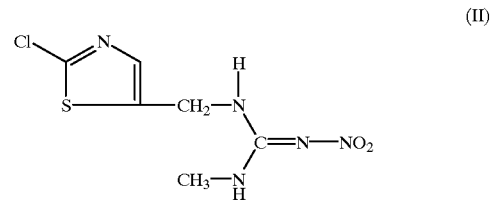

and, especially (E)-1-(2-chlorothiazolyl-5-ylmethyl)-3-methyl-2-nitroguanidine which is E-isomer [hereinafter sometimes referred to briefly as the compound (IIa)] is preferable.

Examples of the salt of the guanidine derivative (I) are agrochemically acceptable salts with an inorganic acid such as hydrochloric acid, hydrobromic acid, hydroiodic acid, phosphoric acid, sulfuric acid or perchloric acid, or an organic acid such as formic acid, acetic acid, tartaric acid, malic acid, citric acid, oxalic acid, succinic acid, benzoic acid, picric acid or p-toluenesulfonic acid.

The above-mentioned guanidine derivative (I) or a salt thereof can be produced in accordance with the per se known method or any method analogous thereto, for example by the processes disclosed in JP-A 28860/1990 and JP-A 157308/1991. Particularly, compound (II) is the compound designated "compound No. 19" in JP-A 157308/1991 and can be produced in accordance with the procedure described in Example 3 in JP-A 157308/1991.

In the agrochemical composition of the present invention, one or more (preferably one to three) species of said guanidine derivative (I) or a salt thereof may be incorporated.

In addition to said guanidine derivative (I) or a salt thereof, the agrochemical composition of the present invention may contain one or more (preferably one to three) other agrochemically active ingredients.

Such agrochemically active ingredients may be insecticides, germicides, etc. as long as they are solid at atmospheric temperature, and specifically the following substances can be mentioned by way of illustration.

[Insecticides]

Pyridafenthion, dimethoate, PMP, CVMP, dimethylvinphos, acephate, salithion, DEP, NAC, MTMC, MIPC, PHC, MPMC, XMC, bendiocarb, pirimicarb, mesomile, oxamyl, thiodicarb, cypermethrin, caltap hydrochloride, thiocyclam, bensultap, diflubenzuron, teflubenzuron, chlorfluazron, buprofezin, hexythiazox, phenbutatin oxide, pyridaben, clofentezine, nitenpyram, etc.

[Germicides]

Thiuram, captan, TPN, phthalide, trichlorophos methyl, phosethyl, methyl thiophanate, benomyl, carbendazole, thiabendazole, diethofencarb, iprodione, vinclozolin, procymidone, fluorimide, oxycarboxin, mepronil, flutolanil, bencyclane, metalaxyl, oxadixyl, triadimefon, hexaconazole, trifolin, blasticidin S, kasugamycin, polyoxin, validamycin A, mildéomycin, PCNB, hydroxyisoxazole, dazomet, dimethirimol, diclomezine, triazine, ferimzone, probenazole, isoprothiolane, tricyclazole, pyroquilone, oxolinic acid, etc.

The above substances are not limited to the above substances but other agrochemicals which are solid at atmospheric temperature can be likewise employed.

The alkenyl group of the alkenylsulfonate for use in the agrochemical composition of the present invention includes a $C_{12-20}$ alkenyl, preferably straight-chain $C_{12-20}$ alkenyl such as palmitoleyl[$CH_3$—$(CH_2)_5CH$=$CH(CH_2)_7$—], oleyl [$CH_3$—$(CH_2)_7CH$=$CH(CH_2)_7$—], vaccenyl[$CH_3$—$(CH_2)_5CH$=$CH(CH_2)_9$—], linoleyl[$CH_3$—$(CH_2)_3(CH_2CH$=$CH)_2(CH_2)_7$—], (9,12,15)-linolenyl[$CH_3$—$(CH_2CH$=$CH)_3(CH_2)_7$—], (6,9,12)-linolenyl[$CH_3$—$(CH_2)_3(CH_2CH$=$CH)_3(CH_2)_4$—] or eleostearyl[$CH_3$—$(CH_2)_3(CH$=$CH)_3(CH_2)_7$—]. Among them, a $C_{14-18}$ alkenyl group, especially a $C_{16-18}$ alkenyl group is preferable. Specifically, various commercial products such as Sorpol 5115 (TOHO Chemical Industry Co., LTD) can be employed.

The salt of the alkenylsulfonate includes alkaline metal salts such as potassium and sodium.

The carrier for use in the agrochemical composition of the present invention may be either of a water-insoluble carrier and a water-soluble carrier, as long as it is solid at atmospheric temperature.

The water-insoluble carrier includes vegetable powders (e.g. soybean flour, tobacco flour, wheat flour, sawdust, etc.), mineral powders (e.g. clay powders such as kaolin, bentonite and acid clay; talc powders such as talc and agalmatolite; silicate powders such as diatomaceous earth and mica), alumina powder, sulfur powder, activated carbon powder, and so on. Particularly preferred is diatomaceous earth.

Diatomaceous earth is available as fossil deposits of one-celled plant diatom, a species of algae growing in both aquatic environments of fresh water and seawater, and is predominantly composed of silicon oxide. Its surface has microscopic pores communicating through geometrically patterned cells and the preferred grade of diatomaceous earth is a highly porous one with diameters about 0.1–1 μm. In the agrochemical composition of the present invention, such diatomaceous earth can be used either as it is or after routine pretreatment for formulation. Thus, powders having a specific surface area of about 1–40 $m^2/g$ as selected from among (1) powder prepared by crushing raw diatomaceous earth, drying the resulting powder, and subjecting the dry powder to size selection, (2) baked powder available on baking the above powder at about 800–1300° C., and (3) baked powder obtained by baking the same together with a flux such as sodium carbonate [Funtai Bussei Zusetsu (Illustrated Powder Properties), Japan Powder Technology Association] can be employed.

Specifically, the dry powder includes various commercial products such as Radiolite SPF (trademark of Showa Chemical Industry co., LTD); the baked powder includes Radiolite #100, Radiolite #200, Radiolite #500, Radiolite #800, and Radiolite Fine Flow B (all trademarks of Showa Chemical Industry co., LTD); and the flux-baked powder includes Radiolite Microfine, Radiolite F, Radiolite Clear Flow, and Radiolite #2000 (all trademarks of Showa Chemical Industry co., LTD). Particularly preferred is diatomaceous earth having a specific surface area of 1–10 $m^2/g$ (for example, the above-mentioned baked and flux-baked powders).

The water-soluble carrier includes water-soluble neutral substances (e.g. lactose, ammonium sulfate, urea, etc.) and water-soluble weakly basic substances (e.g. sodium hydrogen carbonate, sodium thiosulfate, disodium hydrogen phosphate, sodium acetate, sodium carbonate, etc. which have a solubility of not less than 0.05 g/ml in water at 20° C., with the pH of aqueous solutions thereof being about 7–9 at 25° C., regardless of the presence or absence of bound water for hydrate). Preferred are lactose, ammonium sulfate, and sodium hydrogen carbonate. Particularly preferred is lactose.

For lactose, ammonium sulfate, sodium hydrogen carbonate, etc., J.P. (the Pharmacopoeia of Japan) products, industrial grade products, and products of the food additive grade can all be used. Moreover, those substances are preferably within the range of about 0.1–50 μm, in terms of mean particle diameter, with the size range of about 1–20 μm being particularly advantageous. If the particle diameter is larger than the above range, the granulation load tends to make the extrusion procedure difficult by containing with fine particles, thus calling for some additional procedure such as sieving. If the particle diameter is smaller than the above range, the mixing procedure may become difficult.

In preparing the agrochemical composition of the present invention, one or more (preferably one to three) kinds of such carriers can be used.

In addition to the above-mentioned ingredients, the agrochemical composition of the present invention may contain additives which are routinely used in wettable or water-soluble granular agrochemical formulations. For example, surfactants except the alkenylsulfonate as mentioned above, binders, colorants, and antiseptics can be used liberally but selectively depending upon the species of agrochemically active ingredient used.

The surfactant includes nonionic, cationic and anionic surfactants and those surfactants can be used in combination with the alkenylsulfonate as mentioned above.

Also, such a surfactant except the alkenylsulfonate can be used in combination with one or more (preferably one to three) surfactants.

The nonionic surfactant includes polyoxyethylene alkyl ethers, polyoxyethylene alkyl phenyl ethers, polyoxyethylene nonyl phenyl ether, polyoxyethylenepolyoxypropylene ether, polyoxyethylene alkyl esters, sorbitan fatty acid esters, polyoxyethylene sorbitan fatty acid esters, ethylene oxide-propylene oxide block copolymer, and higher fatty acid alkanol amides.

The cationic surfactant includes alkylamine salts and quaternary ammonium salts.

The anionic surfactant includes polymeric compounds such as naphthalenesulfonic acid polycondensate metal salts, naphthalenesulfonateformaldehyde condensates, alkylnaphthalenesulfonates, ligninsulfonic acid metal salts, alkyl allyl sulfonates, alkyl allyl sulfonate sulfates, etc., poly(sodium styrenesulfonate), polycarboxylic acid metal salts, polyoxyethylene distyrenated phenyl ether sulfate ammonium, higher alcohol sulfonates, higher alcohol ether sulfonates, dialkyl sulfosuccinates, and higher fatty acid alkali metal salts.

Among the surfactants mentioned above for the agrochemical composition of the present invention, nonionic surfactants and anionic surfactants are preferred. As to nonionic surfactants, those having HLB numbers from 9 to 18 are preferred in view of water solubility and wettability.

Thus, as such a nonionic surfactant, NP-85 (Daiichi Kogyo Seiyaku, polyoxyethylene nonyl phenyl ether) can be typically mentioned. The preferred anionic surfactant includes naphthalenesulfonic acid polycondensate metal salts, ligninsulfonic acid metal salts, and polycarboxylic acid metal salts.

As commercial products, New Kalgen WG-1 (Takemoto oil & fat co., ltd., naphthalenesulfonic acid polycondensate metal salt), New Kalgen WG-4 (Takemoto oil & fat co., ltd., ligninsulfonic acid metal salt), and New Kalgen WG-5 (Takemoto oil & fat co., ltd., polycarboxylic acid metal salt) are preferred.

As the binder, a water-soluble binder can be used with advantage. The water-soluble binder includes dextrin, polyvinyl alcohol, gum arabic, sodium alginate, polyvinylpyrrolidone, glucose, sucrose, mannitol, and sorbitol. Particularly preferred are dextrin and sucrose. By incorporating such a water-soluble binder, the strength of granules constituting the agrochemical composition of the present invention can be further increased without sacrificing their disintegrability in water or dispersibility in water.

The colorant that can be used includes Cyanine Green G, Eyio Green B400, etc. Such a colorant may be used generally in a water-soluble granular composition of the present invention.

The antiseptic that can be used includes n-butyl p-hydroxybenzoate and potassium sorbate.

The concentration of guanidine derivative (I) or its salt in the agrochemical composition of the present invention is generally about 5–95 weight %, preferably about 10–85 weight %, and for still better results, about 15–80 weight %. More preferred marketing concentration is for example about 16 weight %, about 50 weight %, or about 80 weight %.

Particularly, when the agrochemical composition of the present invention is a wettable granular composition, the concentration of guanidine derivative (I) or a salt thereof in the composition is about 30–85 weight %, preferably about 40–60 weight %, and more preferably about 50 weight %.

On the other hand, when the agrochemical composition of the present invention is a water-soluble granular composition, the concentration of guanidine derivative (I) or a salt thereof in the composition is about 5–60 weight %, preferably about 10–30 weight %, and more preferably about 16 weight %.

When the agrochemical composition of the present invention contain any other agrochemically active ingredients in addition to the guanidine derivative (I) or a salt thereof, the concentration of such other agrochemically active ingredients is generally about 5–95 weight %, preferably about 5–80 weight %, and more preferably about 10–50 weight %.

The proportion of the alkenylsulfonate in the agrochemical composition of the present invention is generally about 0.1–15 weight %, and preferably 1–12 weight %. Particularly, when the agrochemical composition of the present invention is a wettable granular composition, the proportion of the alkenylsulfonate in the composition is about 5–15 weight %, preferably about 7–12 weight %, and more preferably about 10 weight %.

On the other hand, when the agrochemical composition of the present invention is a water-soluble granular composition, the proportion of the alkenylsulfonate in the composition is about 0.1–7 weight %, preferably about 1–5 weight %, and more preferably about 3 weight %.

The proportion of the carrier, e.g. lactose, ammonium sulfate, sodium hydrogen carbonate, and/or diatomaceous earth, in the agrochemical composition of the present invention is generally about 10–95 weight % or preferably about 15–85 weight %. However, the proportion may vary depending upon the concentrations of the agrochemically active ingredient and surfactant.

Particularly, when the agrochemical composition of the present invention is a wettable granular composition, the proportion of the carrier such as a water-insoluble carrier (e.g. diatomaceous earth) is about 10–70 weight %, preferably about 30–50 weight %.

On the other hand, when the agrochemical composition of the present invention is a water-soluble granular composition, the proportion of the carrier such as a water-soluble carrier (e.g. lactose, ammonium sulfate, sodium hydrogen carbonate) is about 25–95 weight %, preferably about 70–90 weight %.

When a surfactant except the alkenylsulfonate is used, the proportion of such a surfactant is generally about 0.1–15 weight % or preferably about 0.1–10 weight % of the total composition.

The binder is used in a proportion of generally 0–20 weight % or preferably 0–10 weight % of the total composition.

The colorant is used in a proportion of generally 0–0.5 weight % or preferably 0–0.3 weight % of the total composition.

The antiseptic is used in a proportion of generally 0–7 weight %, preferably 0.1–5 weight % or more preferably 0.1–3 weight % of the total composition.

The agrochemical composition of the present invention can be classified into a wettable granular agrochemical composition and a water-soluble granular agrochemical composition according to the solubility of the guanidine derivative (I) or a salt thereof and the carrier in water.

(1) When the Carrier is a Water-insoluble Carrier

When the agrochemical composition of the present invention is diluted with water, the carrier is not dissolved but is suspended in diluent water. Therefore, the composition is called the wettable granular agrochemical composition.

(2) When the Carrier is a Water-soluble Carrier (i) The case in which the guanidine derivative (I) or a salt thereof and all other non-carrier ingredients contained therein are dissolved in water when the agrochemical composition of the present invention is diluted with water:

When such an agrochemical composition is diluted with water, all the ingredients are dissolved in water to give an aqueous solution. Therefore, the composition is called a water-soluble granular agrochemical composition.

Such an aqueous solution of the granular agrochemical composition of the present invention is obtained for example when compound (IIa) or a salt thereof is diluted with water to a concentration of generally not over about 300 ppm, preferably not over about 250 ppm, or more preferably not over about 200 ppm.

(ii) The case in which some of the guanidine derivative (I) or a salt thereof and other non-carrier ingredients remains partially undissolved when the agrochemical composition of the present invention is diluted with water:

When such an agrochemical composition is diluted with water, either a portion or the whole of the formulation except for the carrier is not dissolved in water so that a suspension is formed. Therefore, the composition is called a wettable granular agrochemical composition.

For example, when compound (IIa) or a salt thereof is diluted with water to a concentration of generally over about 300 ppm, the agrochemical composition gives a suspension.

The granular agrochemical composition of the present invention can be produced by mixing the guanidine derivative of the formula (I) as mentioned above or a salt thereof and the alkenylsulfonate with a carrier, and granulating the mixture in accordance with the per se known method.

Specifically the granular agrochemical composition of the present invention can be manufactured by the wet extrusion-granulation method which is generally used for the manufacture of wettable or water-soluble granular agrochemical products.

According to the wet granulation method, each 100 parts by weight, on a nonvolatile basis, of the formulation is extrusion-granulated using about 1–30 parts by weight of water. First, the agrochemically active ingredient, surfactant, diluent (volume builder), binder, etc. are uniformly blended by means of a mixer or the like. For example, the solid ingredients are blended to a certain extent and, then, liquid ingredients are added dropwise followed by further mixing. When the solid ingredients are blocks or masses, they are preferably pulverized or comminuted to a suitable particle size so as to facilitate mixing. The preferred particle diameter is about 1–100 $\mu$m. To this mixture is added a suitable amount of water and the whole mixture is further mixed with a kneader. This kneading operation is carried out until the load assumes a sufficiently smooth viscous consistency suitable for the subsequent extrusion. The kneaded mass thus obtained is granulated with a conventional wet extrusion granulator and the resultant granules are dried and sieved to provide the objective granular composition. Sieving operation is generally carried out to the extent that the granules will not pass an approximately 300 $\mu$m-mesh screen but pass through a 1,700 $\mu$m-mesh screen. The preferred diameter range of individual granules is about 0.5–5 mm.

Generally, the bulk density of the wettable or water-soluble granular agrochemical composition of the present invention as thus obtained is preferably about 0.1–1.2 g/ml and more preferably about 0.3–0.8 g/ml.

The agrochemical composition of the present invention comprises safe ingredients and, therefore, is substantially non-phytotoxic and harmless to human and animals during and after application. Therefore, the composition can be used as a safe agrochemical.

The agrochemical composition of the present invention shows good disintegrability in water and has excellent dispersibility in water. Moreover, this agrochemical composition features an improved storage stability of the agrochemically active ingredient without reduction of its water solubility.

The crop plant to which the agrochemical composition of the present invention can be applied includes rice, wheat, barley, sugar beet, maize (Indian corn), cotton, vegetables (e.g. cabbage, Chinese cabbage, radish, cucumber, eggplant, potato, etc.), fruit-bearing trees (e.g. mandarin orange, peach, pear, etc.), tea, and tobacco.

The pest which can be controlled with the agrochemical composition of the present invention includes insects of the order Hemiptera {e.g. cabbage stink bug [*Eurydema rugosum* Motschulsky], black rice stink bug [*Scotinophara lurida* Burmeister], bean bug [*Riptortus clavatus* Thunberg], pear lace-bug [*Stephanitis nashi* Esaki et Takeya], smaller brown planthopper [*Delphacodes striatella* Fallén], brown planthopper [*Nilaparvata lugens* Stal], green rice leafhopper [*Nephotettix bipuntatus cincticeps* Uhler], arrow-head scale [*Prontaspis yanonensis* Kuwana], soybean aphid [*Aphis glycines* Matsumura], turnip aphid [*Rhopalosiphum pseudobrassicae* Davis], cabbage aphid [*Brevicoryne brassicae* Linné], cotton aphid [*Aphis gossypii* Glover], etc.}, the order Lepidoptera {e.g. tabacco cutworm [*Prodenia litura* Fabricius], diamond-back moth [*Plutella maculipennis* Curtis], cabbage butterfly [*Pieris rapae* Linné], Asiatic rice borer [*Chilo suppressalis* Walker], beet worm [*Plusia niarisigna* Walker], oriental tobacco budworm [*Helicoverpa assulta assulta* Guenée], armyworm [*Leucania separata* Walker], cabbage armyworm [*Mamestra brassicae* Linné], smaller tea tortrix [*Adoxophyes orana* Fischer von R öslerstamm] (apple), cotton leaf roller [*Sylepta derogata* Fabricius], grass leaf roller [*Cnaphalocrocic medinalis* Guénée], potato tuberworm [*Phthorimaea operculella* Zeller], tea leaf roller [*Caloptilia theivora* Walsingham], smaller tea tortrix [*Adoxophyes orana* Fischer von R öslerstamm] (tea), etc.}, the order Coleoptera {e.g. potato lady beetle [*Epilachna sparsa orientalis* Dieke], cucurbit leaf beetle [*Rhaphidopalpa femoralis* Motschulsky], striped cabbage flea-beetle [*Phyllotreta vittata* Fabricius], rice leaf beetle [*Oulema oryzae* Kuwayama], rice plant weevil [*Echinocnemus squameus* Billberg], etc.}, the order Diptera {e.g. oriental house fly [*Musca domestica vicina* Macquart], pale house mosquito [*Culex pipiens pallens* Coquillett], common horse fly [*Tabanus trigonus* Coquillett], onion maggot [*Hylemya antiqua* Meigen], seed-corn maggot [*Hylemya platura* Meigen], etc.}, the order Orthoptera {e.g. Asiatic locust [*Locusta migratoria* Linné], African mole cricket [*Gryllotalpa africana* Palisot de Beauvois], etc.}, reticulopterous insects {e.g. German cockroach [*Blattella germanica* Linné], smoky-brown cockroach [*Periplaneta fuliginosa* Serville], etc.}, spider mites {e.g. two-spotted spider mite [*Tetranychus urticae* Koch], citrus red mite [*Panonychus citri* McGregor], Kanzawa spider mite [*Tetranychus kanzawai* Kishida], carmine mite [*Tetranychus telarius* Linné], European red mite [*Panonychus ulmi* Koch], Japanese citrus rust mite [*Aculus pelekassi* Keifer], etc.}, nematodes {e.g. rice white-tip nematode [*Aphelenchoides besseyi* Christie] etc.} and so on.

The recommended method for application depends on the species of the agrochemically active ingredient, the purpose (e.g. insecticide, bactericide), and the crop plant applied, but is generally scattering by means of spraying or dropping, or dipping to field, i.e. paddy field, plow-land, orchard, grassland or non-crop land in accordance with the per se known method. Specifically, spraying can be carried out in the same manner as with the conventional wettable or water-soluble granular agrochemical formulations. Thus, for example, aerial broadcast, soil treatment, folial application, nursery box treatment, hand application along rows, seed dressing, and bed soil mixing can be mentioned. Particularly preferred is folial application.

While the amount of the agrochemical composition of the present invention to be applied depends on the species and concentration of the agrochemically active ingredient, the application site, and the pest or pests to be controlled, the usual dosage for the paddy field and cropland (for tea, wheat, sugar beet, maize, potato, cotton, etc.) pests and orchard pests is about 10–400 g, preferably about 20–300 g, per 10 ares. In terms of the dose of the guanidine derivative (I) or a salt thereof as the agrochemically active ingredient, the recommended dose per 10 ares of a paddy field, cropland, or orchard is about 1–70 g, preferably about 3–50 g. To apply this agrochemical composition, it can be portioned out by weighing or with a volumetric cup, for its weight and volume are well correlated.

The agrochemical composition of the present invention can be applied by the various conventional methods for application of agrochemicals in general. For example, the agrochemical composition is diluted in water when used. The preferred dilution degree is about 100–20000 times (about 1 g/100 ml~1 g/20000 ml).

The application time may be the season of pest hazards, but by applying the agrochemical composition prior to the season, a long-term control effect can be expected.

To avoid infiltration of moisture, the agrochemical composition of the present invention is preferably stored in a moisture-proof container. The moisture-proof container includes plastic bottles, bottles made of polyethylene, polyethylene-aluminum laminate bottles, polyethylene bags, etc.

EXAMPLES

The following examples, reference examples, and test examples are intended to illustrate the present invention in further detail. It should be understood that all parts and percents are by weight, respectively, unless otherwise indicated.

Example 1

| | |
|---|---|
| Compound (IIa) | 16 parts |
| Alkenylsulfonate (Sorpol 5115) | 5 parts |
| Cyanine Green G | 0.15 part |
| Lactose | to make 100 parts |

The above ingredient materials were thoroughly mixed in a mortar and kneaded with 5 parts of tap water. This kneaded mass was granulated with an extrusion granulating machine (Kikusui Seisakusho, LTD., RG-5M) using a 0.8 mm (dia.) sieve to provide cylindrical granules. Those granules were dried at 60° C. for 1 hour to provide a water-soluble granular agrochemical composition containing 16% of compound (IIa).

Example 2

| | |
|---|---|
| Compound (IIa) | 50 parts |
| Alkenylsulfonate (Sorpol 5115) | 10 parts |
| Radiolite #200 | to make 100 parts |

The above ingredient materials were thoroughly mixed in a mortar and kneaded with 25 parts of tap water. The kneaded mass was then treated in the same manner as in Example 1 to provide a wettable granular agrochemical composition containing 50% of compound (IIa).

Example 3

| | |
|---|---|
| Compound (IIa) | 16 parts |
| Alkenylsulfonate (Sorpol 5115) | 3 parts |
| Cyanine Green G | 0.15 part |
| Lactose | to make 100 parts |

The above ingredient materials were thoroughly mixed in a mortar and kneaded with 5 parts of tap water. The kneaded mass was then treated in the same manner as in Example 1 to provide a water-soluble granular agrochemical composition containing 16% of compound (IIa).

Reference Example 1

Using New Kalgen WG-1 in lieu of alkenylsulfonate, the procedure of Example 1 was repeated to provide a water-soluble granular agrochemical composition containing 16% of compound (IIa).

Test Example 1

Using the wettable or water-soluble granular agrochemical compositions prepared in Examples 1–3 and Reference Example 1, disintegrability and dispersibility in water were evaluated by the following methods.

(1) Disintegrability in Water

A hollow cylinder of 500 ml capacity was filled in with 500 ml of water and, then, the sample was added at a final concentration of 100 ppm as active ingredient. The disintegrability of the sample was evaluated on the following 3-grade scale.

A: Not less than ½ of the composition was disintegrated before reaching the bottom.

B: Not less than ½ of the composition remained undisintegrated when it reached the bottom.

C: Not disintegrated at all.

(2) Dispersibility in Water

A hollow cylinder of 500 ml capacity was filled in with 500 ml of water and, then, the sample was added at a final concentration of 100 ppm as active ingredient. The cylinder was placed upside down (180° ×2) in repetition and the dispersion status of the sample was checked after every turn. The number of turnings required for complete dispersion or dissolution was counted.

The results are shown in Table 1.

TABLE 1

| Sample | Disintegrability | Dispersibility |
|---|---|---|
| Ex. 1 | A | 5 |
| 2 | A | 1 |
| 3 | A | 5 |
| Ref. Ex. 1 | C | 19 |

It is clear from Table 1 that the wettable or water-soluble granular agrochemical composition of the present invention is superior to the wettable or water-soluble granular composition not containing any of lactose, ammonium sulfate, sodium hydrogen carbonate, and diatomaceous earth in both disintegrability and dispersibility in water.

INDUSTRIAL APPLICABILITY

The wettable or water-soluble granular agrochemical composition of the present invention which, as described above, has excellent disintegrability in water and excellent dispersibility in water can be used with advantage as an agrochemical composition.

Further, the wettable or water-soluble granular agrochemical composition has excellent granulating ability. For example running time for extrusion granulating may be shortened remarkably.

What is claimed is:

1. A method for improving granulating ability of a granular agrochemical composition, said composition comprising a compound of the formula (II):

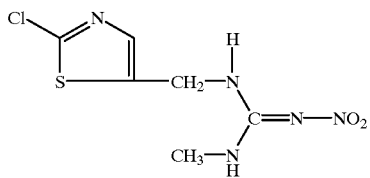

or a salt thereof, said method comprising incorporating in said composition 3 weight % or more of an alkenylsulfonate and a carrier.

2. The method according to claim 1, wherein the alkenylsulfonate is a $C_{12-20}$ alkenylsulfonate.

3. The method according to claim 1, wherein the alkenyl group of the alkenylsulfonate is palmitoleyl[$CH_3$—$(CH_2)_5CH=CH(CH_2)_7$—], oleyl[$CH_3$—$(CH_2)_7CH=CH CH_2)_7$—], vaccenyl[$CH_3$—$(CH_2)_5CH=CH(CH_2)_9$—], linoleyl[$CH_3$—$(CH_2)_3(CH_2CH=CH)_2(CH_2)_7$—], (9, 12, 15)-linolenyl[$CH_3$—$(CH_2CH=CH)_3$—$(CH_2)_7$—], (6,9, 12)-linolenyl[$CH_3(CH_2)_3(CH_2CH=CH)_3(CH_2)_4$—] or eleostearyl[$CH_3$—$(CH_2)_3(CH=CH)_3(CH_2)_7$—].

4. The method according to claim 1, wherein the carrier is one or more carriers selected from the group consisting of lactose, ammonium sulfate, sodium hydrogen carbonate, and diatomaceous earth.

5. The method according to claim 1, wherein said composition comprises 7 to 15 weight % of the alkenylsulfonate based on the total composition.

* * * * *